United States Patent [19]

Gibilisco

[11] Patent Number: 5,178,613
[45] Date of Patent: Jan. 12, 1993

[54] RECESSED TIP FLUID DISPENSER

[75] Inventor: Kenneth J. Gibilisco, Coopersburg, Pa.

[73] Assignee: Merck & Co., Inc., Rahway, N.J.

[21] Appl. No.: 761,557

[22] Filed: Sep. 18, 1991

[51] Int. Cl.$^5$ .................. A61M 35/00; A61J 1/00; B65D 51/18; B67D 3/00

[52] U.S. Cl. .................. 604/294; 604/295; 604/298; 215/206; 215/225; 220/256; 222/546; 222/548; 222/553; 222/556

[58] Field of Search .............. 604/294, 295, 298, 310; 222/546, 548, 553, 556; 215/307, 206, 216, 225; 220/254, 253, 256

[56] References Cited

U.S. PATENT DOCUMENTS

| | | | |
|---|---|---|---|
| 3,029,003 | 4/1962 | Gronemeyer | 222/548 |
| 3,945,381 | 3/1976 | Silver | 128/249 |
| 4,111,200 | 9/1978 | Sbarra et al. | 128/233 |
| 4,500,016 | 2/1985 | Funfstuck | 222/557 |
| 4,733,802 | 3/1988 | Sheldon | 222/181 |
| 4,834,728 | 5/1989 | McKenna | 604/301 |
| 4,941,580 | 7/1990 | Julian | 215/225 |
| 5,040,694 | 8/1991 | Gambello | 220/256 |

OTHER PUBLICATIONS

Hording et al., ACTA Opthalmologica, 60: 213-222 (1982).

Primary Examiner—Randall L. Green
Assistant Examiner—P. Zuttarelli
Attorney, Agent, or Firm—William H. Nicholson; Joseph F. DiPrima

[57] ABSTRACT

A dispenser for liquids, e.g., ophthalmic liquids, is provided with a movable top that rotates to uncover an aperture and to expose a recessed dispensing tip.

16 Claims, 2 Drawing Sheets

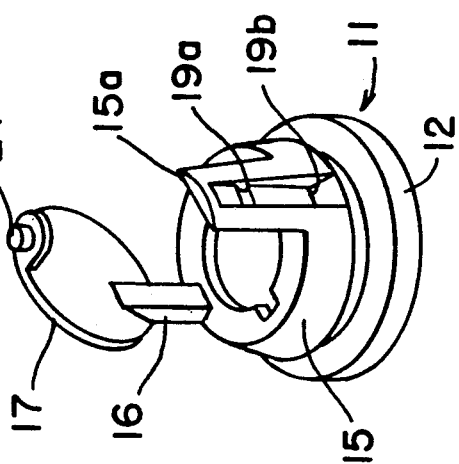
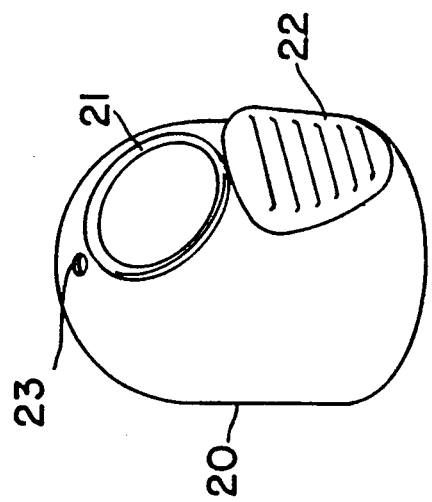
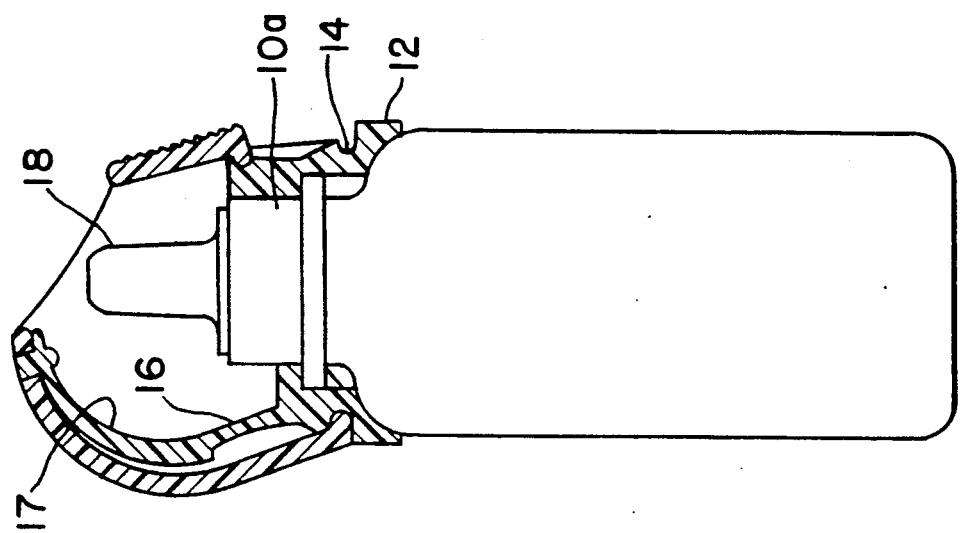
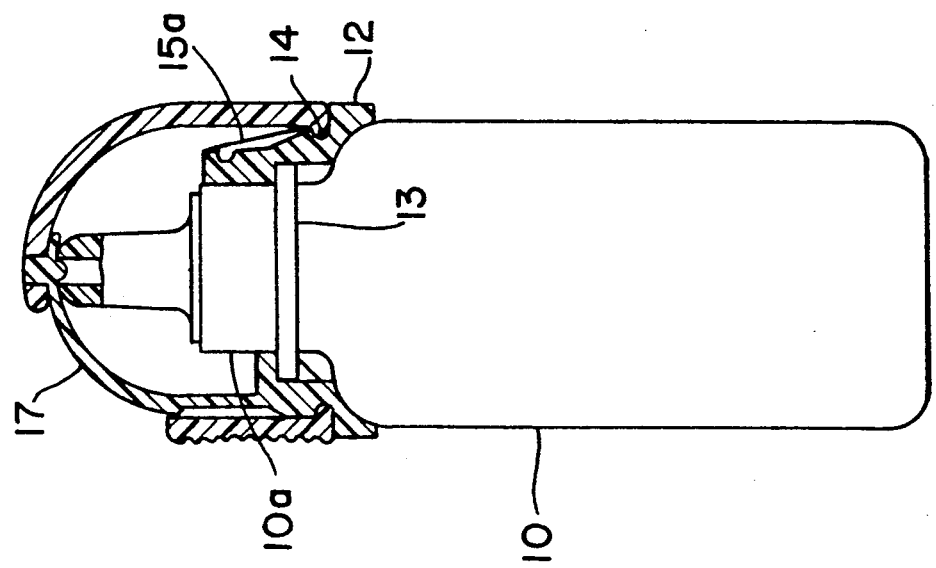

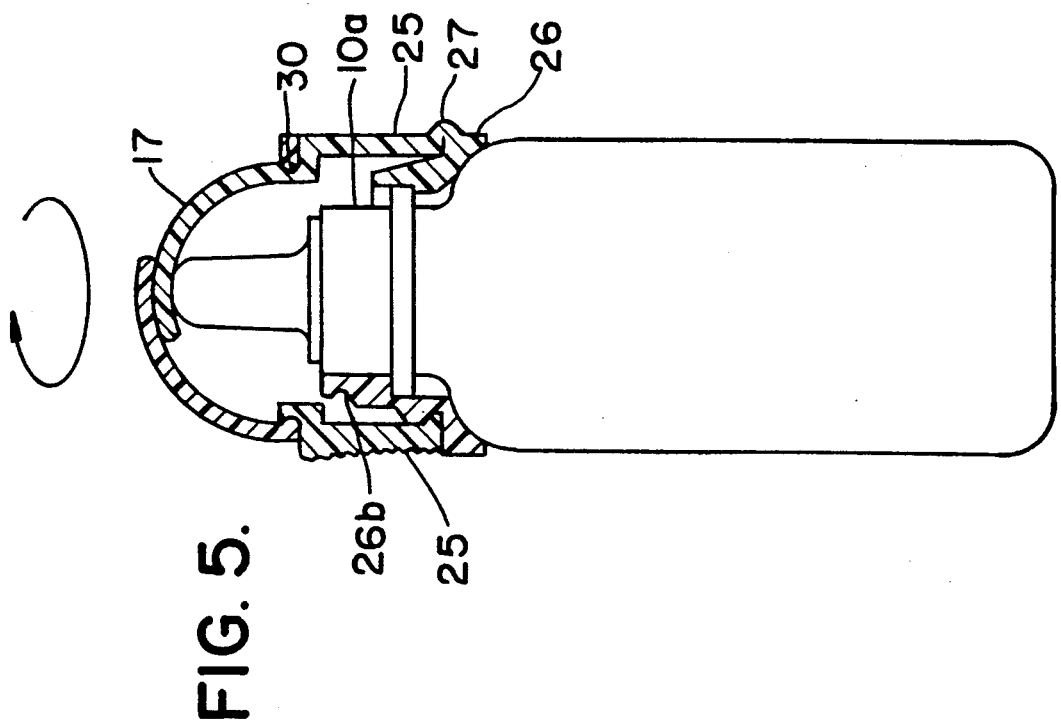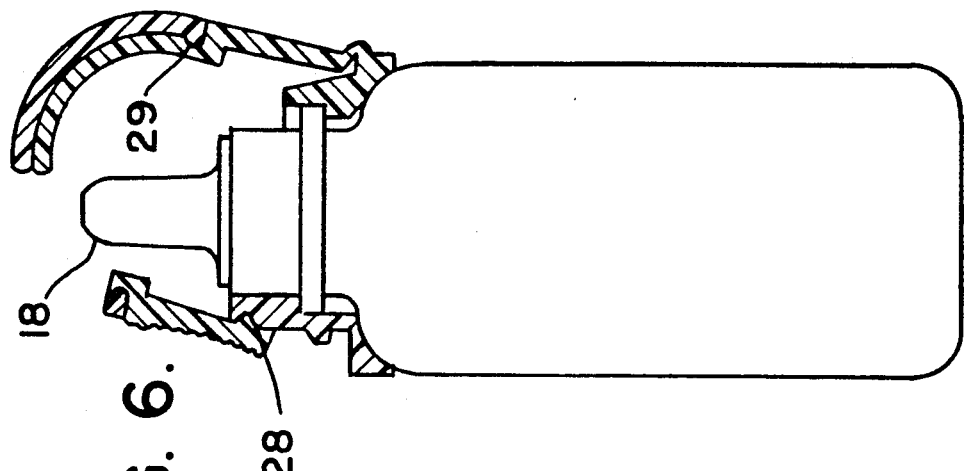

RECESSED TIP FLUID DISPENSER

BACKGROUND OF THE INVENTION

A significant problem with previous devices for dispensing ophthalmic solutions is contamination of the dropper nozzle by inadvertent contact with the eye and other surfaces. The problem is described by Hovding et al., Acta Opthalmologica, 60: 213-222 (1982). This contact also can clog the orifice of the tip, making it impossible to dispense further drops. Contamination of the nozzle can then result in microbial contamination of the solution remaining in the dropper bottle and the transfer of this contamination to either or both eyes.

One common route of this contamination comprises touching the dropper nozzle to the surface of the eye during administration of medication. The contact permits contamination of the fluid remaining in the nozzle, which liquid ultimately flows back into the dropper bottle, contaminating the entire contents, and sometimes eventually plugging the dispenser tip.

Some devices have been reported which serve to prevent contact of a dropper nozzle but which were designed primarily to aid in aiming the dropper nozzle properly. See for example U.S. Pat. Nos. 4,834,728; 3,945,381; 4,111,200 and 4,733,802. These devices generally comprise a large cup-shaped or cone-shaped member, the rim of which rests on the patient's face over the eye socket and have a tip composed of a nozzle protruding through the cup-shaped member oriented so that drops from the nozzle will enter the eye.

These reported devices are fairly large, cumbersome and not easily carried in a handbag or pocket. The diameter of the cup-shaped member is large enough to permit easy contact of the dropper tip with fingers or other septic objects resulting in contamination of the device and its contents. Furthermore, covering of the eye with the large cup-shaped member may actually increase the blink reflex, thus raising the likelihood that the drop will miss the intended target.

OBJECTS OF THE INVENTION

It is an object of the present invention to provide a fluid dispensing device having a movable top that rotates to uncover an aperture and to expose a recessed dispensing tip within the aperture. A further object is to provide a fluid dispensing device having a top with restricted movement that locks in both open and closed positions. Another object is to provide a fluid dispensing device wherein the dispensing tip is always maintained below the plane of the aperture. Still another object is to provide a fluid dispensing device that may be easily opened and closed by patients having limited or impaired manual dexterity. These and other objects of the present invention will be apparent from the following description.

SUMMARY OF THE INVENTION

A fluid dispensing device is provided with a movable top that rotates to uncover an aperture and to expose a recessed dispensing tip within the aperture. Reversing the rotation of the top covers the aperture and conceals the dispensing tip.

BRIEF DESCRIPTION OF THE DRAWINGS

FIG. 1 is a cross-section of a side elevation of the recessed tip fluid dispenser of the present invention in closed position, FIG. 2 is a cross-section of a side elevation of the recessed tip fluid dispenser of the present invention in open position, FIG. 3 is a perspective view of the inner top, and FIG. 4 is a perspective view of the outer top.

FIGS. 5 and 6 are cross-sectional views of another embodiment of the present invention in closed and open position, respectively.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

The fluid dispensing device of the present invention is intended for delivery of sterile fluids such as opthalmic fluids intended for administration to the eye, or sterile fluids intended for administration to any bodily surface. The fluid dispensing device of the present invention has recessed dispensing means so that fluids can be dispensed without the dispensing means contacting the surface to which the fluids are administered.

The fluid dispensing means of the present invention consists of a bottle 10 which can be formed from a variety of materials such as, for example, soft or hard plastic, e.g., polypropylene or low density polyethylene, or other manually deformable material, or glass. The bottle, if made of plastic, can be produced by conventional blow molding technique. It is to be understood that the bottle of the present invention is not limited to any specific material or to its manufacture by any specific process as it will be understood by those skilled in the art that many different materials and various manufacturing techniques can be employed.

Bottle 10 is adapted to contain a liquid medication, preferably a physiologically acceptable, liquid ophthalmic medication. The upper portion of the bottle 10 has neck 10a that is tapered to provide a dispenser tip 18. Tip 18 has an internal channel communicating with the bottle (not shown as obvious) and can be calibrated to deliver a predetermined amount of liquid.

Inner cap 11 (FIG. 3) has lower flange member 12 that is snap fitted over transfer bead 13 and is keyed to bead 13 to prevent rotation around neck 10a (not shown as obvious). Flange 12 has a circumferential groove 14 and wall 15 above groove 14. Wall 15 has member 16 which joins shield 17 to wall 15. One part of wall 15 is built up to form wall 15a having indents 19a and 19b. An overcap 20 having aperture 21 and thumb rest 22 is adapted to fit over inner cap 11 and to snap into and to rotate in groove 14. Overcap 20 also is adapted to pivot in groove 14. The top of overcap 20 is provided with a recess or opening 23 adapted to receive projection 24 on shield 17 to maintain shield 17 in desired position within overcap 20. Overcap 20 also is provided with two beads (not shown as obvious) on inner surface of overcap 20 that cooperate with indents 19a and 19b to limit its pivoting movement.

When overcap 20 is closed aperture 21 sits over shield 17, whereby dispensing tip 18 is not only concealed but protected from contamination by dust, dirt or any other source of contamination. When overcap 20 is rotated (a stop, not shown as obvious prevents over rotation) so that aperture 21 does not sit over aperture 21, dispensing tip 18 is exposed and, by pivoting overcap 20 upwardly, tip 18 is centered in aperture 21 whereby the contents of bottle 10 are ready to be dispensed. At all times that tip 18 is exposed, however, it is always recessed below the plane of aperture 21 and so protected from accidental contamination. Since overcap 20 does not have to be removed to uncover aperture 21, it is impossible to drop or lose the overcap.

In another embodiment of the present invention, shown in FIGS. 5 and 6, shield 17 is attached to upper portion of ring 25 that is keyed to flange 26 on neck 10a to prevent rotation around neck 10a. Ring 25 is joined to flange 26 by hinge means 27. One side of flange 26 is built up around neck 10a and has an indent 26b that cooperates with a bead 28 on inner surface of ring 25 to stop pivoting movement of ring 25. An overcap 20 is snapped into outside groove 29 in upper region of ring 25 and held in place by bead 30 on inner surface of overcap 20. In closed position, shown in FIG. 5, shield 17 closes aperture 21. Rotating overcap 20 as shown in FIG. 6 moves aperture 21 away from shield 17 to expose dispensing tip 18. By pivoting overcap 20 upwardly, tip 18 is centered within aperture 21 for accurate dispensing of contents.

What is claimed is:

1. A container for storing and dispensing a liquid comprising a body having a neck and a dispensing tip, an inner cap having a top and a shield member without an aperture fixed to the body, and an over cap having an aperature through which dispensed liquid passes, the over cap being adjustably mounted to the inner cap such that said overcap can be rotated about the longitudinal axis and pivoted about the transverse axis of the inner cap, the shield member being of a size adequate to cover the aperature when the aperature is over the shield member.

2. A container according to claim 1 wherein the inner cap is immovable relative to the body.

3. A container according to claim 2 wherein the inner cap is rendered immovable relative to the body by key means.

4. A container according to claim 1 wherein the inner cap is provided with a circumferential groove.

5. A container according to claim 4 wherein the overcap is adapted to fit into and to rotate in the circumferential groove.

6. A container according to claim 1 wherein the inner cap is provided with a flange adapted to attach the inner cap to the body.

7. A container according to claim 6 wherein the flange of the inner cap is attached to a transfer bead on the body.

8. A container according to claim 1 wherein the shield member is attached to the top of the inner cap.

9. A container according to claim 1 wherein the inner cap is provided with a wall having stop means to restrict upward pivoting movement of the overcap.

10. A container according to claim 1 wherein the overcap is provided with means to lock the overcap in a closed position.

11. A container according to claim 1 wherein the overcap contains guide means for the shield member.

12. A container according to claim 1 wherein the shield member and the overcap are provided with means that cooperate to maintain the shield in desired position within the overcap.

13. A container according to claim 12 wherein the cooperating means comprises a recess in the top of the overcap adapted to receive a projecting member on the shield member.

14. A container according to claim 12 wherein the cooperating means comprises an opening in the top of the overcap adapted to receive a projecting member on the shield member.

15. A container according to claim 12 wherein the cooperating means comprises a projecting member on the shield member.

16. A container according to claim 1 wherein rotation of the overcap exposes the dispensing tip and wherein pivotting of the dispensing tip centers the dispensing tip in the aperture.

* * * * *